United States Patent [19]

Hasegawa et al.

[11] Patent Number: 5,068,235
[45] Date of Patent: Nov. 26, 1991

[54] DIAZABICYCLOALKANE DERIVATIVE

[75] Inventors: Etsuo Hasegawa, Omiya; Akihiro Kawaguchi, Honjo; Makoto Kajitani, Saitama; Mitsugi Yasumoto, Honjo; Nobuo Kasahara; Junji Yamamoto, both of Tokushima, all of Japan

[73] Assignee: Taiho Pharmaceutical Company, Limited, Tokyo, Japan

[21] Appl. No.: 566,456

[22] PCT Filed: Dec. 27, 1989

[86] PCT No.: PCT/JP89/01316
§ 371 Date: Aug. 16, 1990
§ 102(e) Date: Aug. 16, 1990

[87] PCT Pub. No.: WO90/07509
PCT Pub. Date: Jul. 12, 1990

[30] Foreign Application Priority Data

Dec. 28, 1988 [JP] Japan .................. 63-335159

[51] Int. Cl.⁵ .................. A61K 31/505; A61K 31/44; A61K 31/415; C07D 515/02
[52] U.S. Cl. ................................ 514/258; 514/300; 514/387; 544/282; 546/121; 548/302
[58] Field of Search ............... 544/282; 548/181, 302; 546/121; 514/258, 300, 365, 387

[56] References Cited

PUBLICATIONS

Arch. Pharm., vol. 294 (1961), K. Winterfeld et al., [Reactivity of 2-Aza-3-Oxoindolizidine], pp. 404–410.
Chem. Letter, No. 6 (1975), M. Watanabe et al., [Azafulvenes. 1. Novel Generative Method of 6-Amino-1-Azafulvene and its Cycloaddition Reaction with Isothiocycanate], pp. 607–610.

Primary Examiner—Mukund J. Shah
Assistant Examiner—Matthew V. Grumbling
Attorney, Agent, or Firm—Armstrong, Nikaido, Marmelstein, Kubovcik & Murray

[57] ABSTRACT

The present invention provides a diazabicycloalkane derivative which has the following formula and is useful as medicaments for treating senile dementia, i.e., as cerebral function improving agents and cerebral metabolism activators or anoxic brain damage protectives

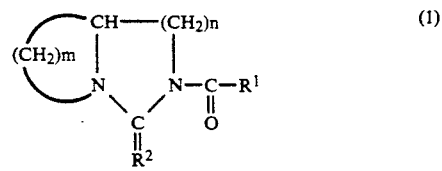

wherein $R^1$ is phenyl group, thiazolyl group or furyl group, the phenyl group may have lower alkoxy, lower alkyl or halogen atom as a substituent, $R^2$ is oxygen atom or sulfur atom, m is 3 or 4, n is 1 or 2.

9 Claims, No Drawings

DIAZABICYCLOALKANE DERIVATIVE

TECHNICAL FIELD

The present invention relates to a diazabicycloalkane derivative which is novel compound and is not disclosed in the literature. The present compound has a cerebral function improving effect, a cerebral metabolism activating effect and is effective against senile dementia.

BACKGROUND ART

With an increase in the population of advanced ages in recent years, patients with senile dementia increase in number, posing a serious problem medically and socially. Although various antidementia drugs have been investigated and developed in view of the situation, no compounds have been provided with satisfactory efficacy.

An object of the present invention is to provide novel diazabicycloalkane derivatives which are very useful as medicaments for treating senile dementia, i.e., as cerebral function improving agents and cerebral metabolism activators or anoxic brain damage protectives.

DISCLOSURE OF THE INVENTION

The present invention provides a diazabicycloalkane derivative represented by the formula

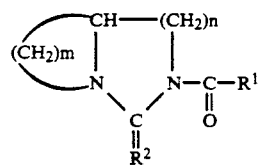

wherein $R^1$ is phenyl group, thienyl group or furyl group, the phenyl group may have lower alkoxyl, lower alkyl or halogen atom as a substituent, $R^2$ is oxygen atom or sulfur atom, m is 3 or 4, n is 1 or 2.

In the invention, examples of lower alkoxyl groups, which are a substituent for the phenyl group represented by $R^1$, are a straight-chain or branched-chain alkoxyl group having 1 to 6 carbon atoms such as methoxy, ethoxy, n-propoxy, isopropoxy, n-butoxy, isobutoxy, sec-butoxy, t-butoxy, n-pentyloxy, isopentyloxy and hexyloxy group. Lower alkyl group means a straight-chain or branched-chain alkyl group having 1 to 6 carbon atoms such as methyl, ethyl, n-propyl, isopropyl, n-butyl, isobutyl, sec-butyl, t-butyl, n-pentyl, isopentyl and hexyl group. Examples of halogen atoms are fluorine, chlorine, bromine and iodine. When $R^1$ represents a substituted phenyl group, the group preferably has 1 to 3 substituents.

Among the compounds of the formula (1), preferable are those wherein $R^1$ is a phenyl group having or not having 1 to 3 substituents selected from among lower alkoxyl, lower alkyl and halogen atom. More preferable are compounds of the formula (1) wherein $R^1$ is a phenyl group having one lower alkoxyl as a substituent, m is 3 and n is 2.

Further, we have found that the present compound of the formula (1) has an excellent cerebral function improving effect, cerebral metabolism activating or anoxic brain damage protecting effect and is effective against senile dementia.

Accordingly, the present invention provides a cerebral function improving composition and a cerebral metabolism activating or anoxic brain damage protecting composition each comprising an effective amount of a compound of the formula (1) and a pharmacologically acceptable carrier.

The present invention further provides a method of improving cerebral functions and activating cerebral metabolism or protecting anoxic brain damage characterized by administering an effective amount of a compound of the formula (1).

The compounds of the formula (1) have pharmacological activities to ameliorate:

(1) cerebral damage in anoxia, and
(2) amnesia induced by scopolamine in passive condition avoidance response.

These pharmacological properties are useful for activating injured nervous cells and ameliorate memory and learning disturbances.

Accordingly, the compounds of the present invention are usable not only as medicaments for use in treating deterioration of intelligence or neurasthenia, ammnesia, senile dementia or intellectual fatigue, cerebrovascular dementia, aftereffects of encephalopathy and Alzheimer's disease but also as medicaments for improving other cerebral functions or for activating cerebral metabolism or protecting anoxic brain damage.

The diazabicycloalkane derivative (1) of the present invention can be prepared, for example, by the following reaction processes.

a) Diazabicycloalkanone

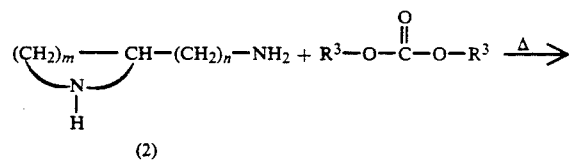

(2)

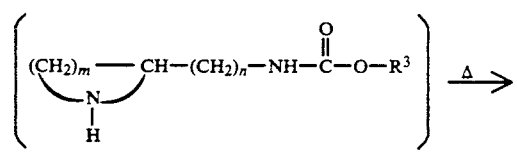

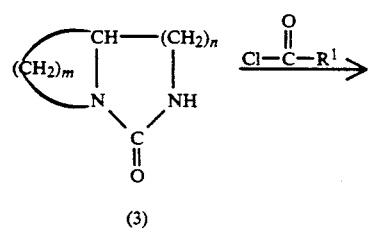

(3)

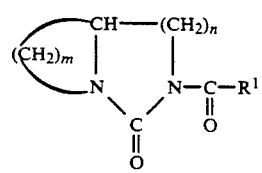

b) Diazabicycloalkanethione

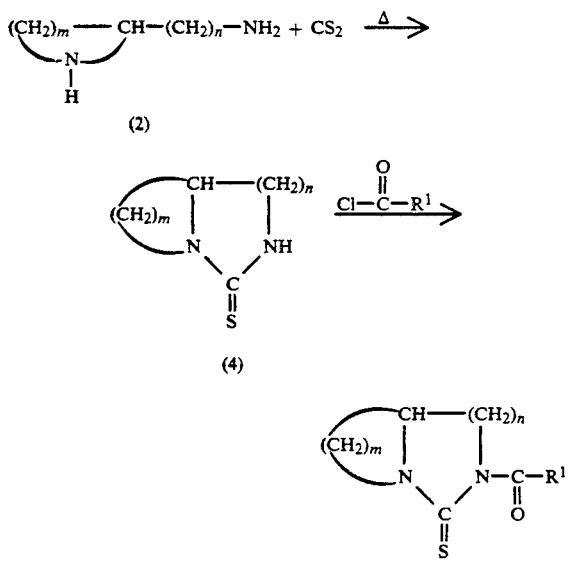

wherein $R^1$, m and n are same as above, $R^3$ is methyl or ethyl.

Namely, the present compound is prepared by reacting a diazabicycloalkanone or diazabicycloalkanethione of the formula (5) with an acid chloride of the formula (6), in a solvent, preferably in the presence of a base,

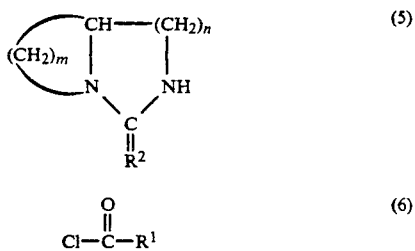

wherein $R^1$, $R^2$, m and n are same as above.

Among the compounds of the formula (5), diazabicycloalkanone [formula (3)] can be prepared by the following manner.

2-($\epsilon$-Aminoalkyl)piperidine or 2-($\epsilon$-aminoalkyl)pyrrolidine of the formula (2)

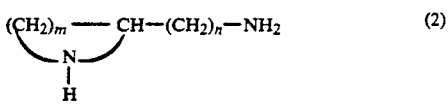

wherein m and n are same as above, is mixed with an excess of dimethyl carbonate or diethyl carbonate without a solvent and the mixture is refluxed with heating. The excess of dimethyl carbonate or diethyl carbonate is removed by distillation under reduced pressure, and the resulting residue is further heated. The solid product obtained by cooling is washed by adding thereto a suitable solvent such as diethyl ether and then recrystallized to give a desired diazabicycloalkanone.

Among the compounds of the formula (5), diazabicycloalkanethione [formula (4)] can be prepared, for example, by the following manner. Namely, the compound of the formula (4) can be prepared by reacting the amine of the formula (2) with carbon disulfide according to the method by J. H. Gogerty disclosed in Journal of Medicinal Chemistry, 14, 878 (1971).

As to the proportion of the compound (5) and the compound (6), it is usual to use 0.5 to 2 moles, preferably one mole of the compound (6) per mole of the compound (5). Examples of bases are triethylamine and pyridine. The amount of the base is usually 0.5 to 2 moles, preferably one mole per mole of the compound (6).

The solvent is not limited specifically insofar as it does not participate in the reaction. Examples of solvents generally useful are ethers such as ethyl ether and tetrahydrofuran, hydrocarbon halides such as methylene chloride and chloroform, aromatic hydrocarbons such as benzene and toluene, aprotic polar solvents such as N,N-dimethylformamide. The reaction temperature is 0° to 150° C., preferably 30° to 70° C. The reaction time is 1 to 24 hours, preferably 2 to 10 hours.

The present compound can be readily purified or isolated by a usual separating method, such as extraction, concentration, distillation, recrystallization, column chromatography or the like.

When the present compound is to be administered for the purpose of treating deterioration of intelligence or neurasthenia, amnesia, senile dementia or intellectual fatigue, and Alzheimer's disease, the compound is administered in the form of a pharmacological preparation such as oral preparation, injection, suppository or the like. These preparations can be produced by conventional methods already known to those skilled in the art.

Solid preparations for oral administration can be produced in a usual manner by adding to the present compound an excipient, and when required, a binder, disintegrator, lubricant, coloring agent, corrigent, flavor and the like, and making the mixture into tablets, granules, powders or an encapsulated preparation. Such additives are those generally used in the art. Examples of useful excipients are lactose, sucrose, sodium chloride, glucose, starch, calcium carbonate, kaolin, microcrystalline cellulose, silicic acid and the like. Examples of useful binders are water, ethanol, propanol, syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like. Examples of useful disintegrators are dried starch, sodium alginate, agar powder, sodium hydrogen carbonate calcium carbonate, sodium laurylsulfate, stearic acid monglyceride, starch, lactose and the like. Examples of useful lubricants are purified talc, stearic acid salts, borax, polyethylene glycol and the like. Examples of useful corrigents are sucrose, bitter orange peel, citric acid, tartaric acid and the like.

Liquid preparations for oral administration can be produced by adding a corrigent, buffer, stabilizer, flavor and the like to the present compound, and making the mixture into a liquid oral preparation, syrup, elixir or the like. Examples of useful corrigents are those exemplified above. Exemplary of useful buffers are sodium citrate and the like. Examples of useful stabilizers are tragacanth, gum arabic, gelatin and the like.

Injections can be produced in a usual manner by adding a pH adjusting agent, buffer, stabilizer, isotonic agent, local anesthetic and the like to the present compound, and formulating the mixture into a preparation for subcutaneous, intramuscular or intravenous injection. Examples of useful pH adjusting agents and buffers are sodium citrate, sodium acetate, sodium phosphate and the like. Examples of useful stabilizers are sodium pyrosulfite, EDTA, thioglycolic acid, thiolactic acid and the like. Examples of useful local anesthetics are procaine hydrochloride, lidocaine hydrochloride and the like.

Suppositories can be prepared by adding to the present compound a pharmaceutical carrier known in the art, such as polyethylene glycol, lanolin, cacao fat, fatty acid triglyceride or the like, along with Tween (registered trademark) or like surfactant and the like when desired, and treating the mixture in the usual manner.

Although the amount of the present compound to be contained in the unit form of each preparation varies with the symptoms of the patient, the type of preparation, etc., the amount is generally preferably about 1 to about 300 mg for oral administration, about 1 to about 50 mg for injection or about 1 to 200 mg for suppositories, per unit of the preparation. The dosage of the compound to be given in the form of such a preparation can not be determined specifically but varies with the symptoms, weight, age, sex, etc. of the patient. However, it is given usually at a dose of about 0.5 to about 1000 mg, preferably 1 to 500 mg, per day for adults, preferably once or in up to four divided doses.

BEST MODE FOR CARRYING OUT THE INVENTION

The present invention will be described below in greater detail with reference to examples wherein diazabicycloalkane derivatives of the formula (1) were prepared, and to the tests conducted to determine the antiamnesia activity of compounds (1) and the acute toxicity test thereof. Table 1 shows the compounds prepared in the examples. In the elementary analysis in the Table, upper column shows analyzed value, lower column calculated value.

EXAMPLE 1

To 22 g (193 mmole) of 2-(2-aminoethyl)pyrrolidine [W. Schuett, H. Rapoport, Journal of American Chemical Society, 84, 2266 (1962)] was added 200 ml of diethyl carbonate and the mixture was refluxed on an oil bath at 135° C. for 24 hours, and then excess of diethyl carbonate was removed under reduced pressure. The residue was further heated for one hour and then cooled. The resulting solid was triturated with 0.3 l of ether. The insolubles were collected by filtration and washed with ether. The insolubles were suspended again in 0.3 l of ether and the suspension was refluxed with heating. Thereto was added a small amount of methylene chloride to dissolve the insolubles and the solution was subjected to recrystallization by cooling with ice. The precipitates were collected by filtration and washed with a small amount of ether. The precipitates were dried in vacuo to obtain 14.8 g (yield 55%) of hexahydropyrrolo[1,2-c]pyrimidine-1-(12H)-one (melting point 123°~124° C.).

In 30 ml of dry methylene chloride were dissolved 1.6 g (11.4 mmole) of hexahydropyrrolo[1,2-c]pyrimidine-1-(12H)-one obtained in the above and 1.95 g (11.4 mmole) of p-methoxybenzoyl chloride. To the solution was added dropwise with stirring under cooling a solution of 1.39 g (13.7 mmole) of dry triethylamine in 5 ml of dry methylene chloride. After stirring at room temperature for 30 minutes, the mixture was refluxed with heating for 3 hours. After cooling, 10 ml of water was added and the mixture was stirred for 5 minutes, and thereto was added 0.25 l of ethyl acetate. An organic layer was washed with water, saturated aqueous sodium bicarbonate, water and saturated aqueous sodium chloride in this order and then dried over anhydrous magnesium sulfate. The solvent was removed under reduced pressure and the residue was purified by silica gel column chromatography (eluent: ethyl acetate) to collect a desired product. The solvent was removed under reduced pressure and the residue was recrystallized from ethanol/hexane to obtain 2.10 g (yield 67.2%) of the desired hexahydropyrrolo[1,2-c]pyrimidine-2-(4-methoxybenzoyl)-1-(12H)-one. Table 1 shows melting point and elementary analysis.

EXAMPLES 2 TO 6

Compounds 2 to 6 were prepared in the same manner as in Example 1. Table 1 shows the physical data.

EXAMPLE 7

Compound 7 was prepared in the same manner as in Example 1 with the exception of using a compound of the formula (3) in which m=3 and n=1 as a starting compound. Table 1 shows the physical data.

EXAMPLE 8

Compound 8 was prepared in the same manner as in Example 1 with the exception of using a compound of the formula (3) in which m=4 and n=1 as a starting compound. Table 1 shows the physical data.

EXAMPLE 9

Compound 9 was prepared in the same manner as in Example 1 with the exception of using a compound of the formula (3) in which m=4 and n=2 as a starting compound. Table 1 shows the physical data.

EXAMPLE 10

To a solution of 3.0 g of 2-(2-aminoethyl)pyrrolidine in 20 ml of dry pyridine was added 3.2 g of carbon disulfide dropwise at room temperature. The resulting mixture was stirred at the same temperature for 5 hours. After removing the solvent under reduced presure, 1 l of ether was added to the residue and the mixture was refluxed. To a filtrate obtained by hot filtration was added 2 l of hexane and the mixture was subjected to recrystallation with ice-cooling to obtain 1.74 g (yield 43%) of hexahydropyrrolo[1,2-c]pyrimidine-1-(12H)-thione (melting point 129°~131° C.).

A mixture of 1.78 g (11.5 mmole) of hexahydropyrrolo[1,2-c]pyrimidine-1-(12H)-thione, 1.96 g (11.5 mmole) of p-methoxybenzoyl chloride and 1.91 g (13.8 mmol) of triethylamine in 50 ml of dry methylene chloride was refluxed for 23 hours. The mixture was treated in the same manner as in Example 1 to obtain 2.12 g (yield 63%) of the desired hexahydropyrrolo[1,2-c]pyrimidine-2-(4-methoxybenzoyl)-1-(12H)-thione. Table 1 shows melting point and elementary analysis.

EXAMPLE 11

| Compound 1 | 200 mg |
| Lactose | 500 mg |
| Corn starch | 280 mg |
| Hydroxypropyl cellulose | 20 mg |

The above ingredients in the proportions given were made into a granular preparation by the usual method in an amount of 1000 mg per wrapper.

EXAMPLE 12

| Compound 1 | 100 mg |
|---|---|
| Lactose | 85 mg |
| Microcrystalline cellulose | 50 mg |
| Hydroxypropyl starch | 30 mg |
| Talc | 4 mg |
| Magnesium stearate | 1 mg |

By the usual method, the above ingredients in the proportions given were made into tablets each weighing 270 mg.

EXAMPLE 13

| Compound 10 | 100 mg |
|---|---|
| Lactose | 50 mg |
| Potato starch | 50 mg |
| Microcrystalline cellulose | 109 mg |
| Magnesium stearate | 1 mg |

By the usual method, the above ingredients in the proportions given were made into an encapsulated preparation in an amount of 310 mg in each capsule.

EXAMPLE 14

| Compound 7 | 250 mg |
|---|---|
| Fatty acid triglyceride | 750 mg |

By the usual method, the above ingredients in the proportions given were made into suppositories each weighing 1000 mg.

EXAMPLE 15

| Compound 2 | 5 mg |
|---|---|
| Sodium chloride | 18 mg |
| Distilled water for injections, suitable amount | |

The above ingredients in the proportions given were made into an injection by the usual method.

TEST EXAMPLE 1

Reversal activity of amnesia

1. Animals

Groups of 6 to 16 rats (Wistar, males, weighing 170 to 240 g) were used for the experiment.

2. Drug

Scopolamine was used as dissolved in physiological saline, and the test compound as dissolved or suspended in 0.5% solution of sodium carboxymethyl cellulose.

Scopolamine was subcutaneously given at a dose of 0.5 mg/kg 30 minutes before aquisition trials. The test compound was orally given immediately after the aquisition trials.

3. Method

A step-through passive avoidance apparatus was used with reference to Psychopharmacology, 78, 104~111 (1982) and Japan Journal of Pharmacology, 37, 300~302 (1985). The apparatus consisted of a dark compartment (25×12×30 cm) having a grid serving as a floor, and a light compartment (25×12×12 cm) illuminated with 20-W daylight fluorescent lamp from above and separated from the dark compartment by a guillotine door. The rat was subjected to habituation trials about 1 hour before aquisition trials. The habituation was accomplished by placing the rat into the light compartment, opening the door 5 seconds thereafter, closing the door when the four legs completely entered the dark compartment, leaving the rat in the dark compartment for 10 seconds and thereafter taking out the rat. The acquistion trial was accomplished in the same manner as the habituation 1 hour thereafter except that simultaneously when the door was closed upon the movement of the rat into the dark compartment, an unescapable foot shock of 4.5 mA was given to the rat by the floor grid for 1 second.

A retention test was conducted 24 hours after the aquisition trials to measure the step-through latency during which the rat placed into the light compartment remained therein before moving into the dark compartment, i.e., the duration of a passive avoidance reaction. For a rat exhibiting the avoidance reaction for more than a maximum period of time measured (300 seconds), 300 seconds was recorded.

The results were given by amnesia reversal (%) represented by the formula below which was described in J. Med. Chem. vol. 27 684~691 (1984).

$$\text{amnesia reversal } (\%) = \frac{\text{drug group} - \text{base-line control group}}{\text{ceiling control group} - \text{base-line control group}} \times 100$$

drug group: step-through latency (second) of the group administered with scopolamine and the test compound base-line control group: step-through latency (second) of the group administered with scopolamineceiling control group: step-through latency (second) of the control group (max.; 300 seconds)

Table 2 shows the results in which Compound 1 and Compound 10 were used. As a control was used Aniracetam which was investigated and considered effective in the present clinical fields. It is apparent from Table 2 that present compound exhibits excellent antiamnesia effect compared with Aniracetam in a dose of 1/10 to 1/30 of that of the latter.

TABLE 1

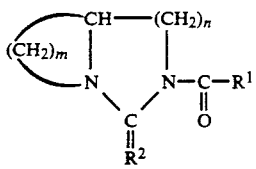

| Compd. No. | $R^2$ | m | n | $R^1$ | m.p. (°C.) | Yield (%) | Formula | C | H | N |
|---|---|---|---|---|---|---|---|---|---|---|
| 1 | O | 3 | 2 | −⟨⟩−OCH₃ | 86~88 | 67 | $C_{15}H_{18}N_2O_3$ | 65.59 / 65.68 | 6.82 / 6.61 | 10.14 / 10.21 |
| 2 | O | 3 | 2 | −⟨⟩ | 93~94 | 82 | $C_{14}H_{16}N_2O_2$ | 68.89 / 68.83 | 6.73 / 6.60 | 11.47 / 11.47 |
| 3 | O | 3 | 2 | −⟨⟩−Cl | 125~126 | 90 | $C_{14}H_{15}N_2O_2Cl$ | 60.33 / 60.33 | 5.11 / 5.42 | 10.01 / 10.05 |
| 4 | O | 3 | 2 | −⟨⟩−CH₃ | 129~130 | 63 | $C_{15}H_{18}N_2O_2$ | 69.78 / 69.75 | 7.18 / 7.02 | 10.88 / 10.84 |
| 5 | O | 3 | 2 | −⟨S⟩ | 96~98 | 50 | $C_{12}H_{14}N_2O_2S$ | 57.49 / 57.58 | 5.72 / 5.64 | 11.00 / 11.19 |
| 6 | O | 3 | 2 | −⟨O⟩ | 105~107 | 60 | $C_{12}H_{14}N_2O_3 \cdot 1/5H_2O$ | 60.61 / 60.60 | 5.99 / 6.10 | 11.66 / 11.78 |
| 7 | O | 3 | 1 | −⟨⟩−OCH₃ | 75~77 | 69 | $C_{14}H_{16}N_2O_3$ | 64.72 / 64.60 | 6.48 / 6.20 | 10.72 / 10.76 |
| 8 | O | 4 | 1 | −⟨⟩−OCH₃ | 125.5~126.5 | 58 | $C_{15}H_{18}N_2O_3$ | 65.54 / 65.68 | 6.74 / 6.61 | 10.13 / 10.21 |
| 9 | O | 4 | 2 | −⟨⟩−OCH₃ | 88~89 | 60 | $C_{16}H_{20}N_2O_3$ | 66.43 / 66.65 | 7.10 / 6.99 | 9.58 / 9.72 |
| 10 | S | 3 | 2 | −⟨⟩−OCH₃ | 117~118 | 63 | $C_{15}H_{18}N_2O_2S$ | 61.79 / 62.04 | 6.20 / 6.25 | 9.56 / 9.65 |

TABLE 2

| | Dose (mg/kg) | | | | | |
|---|---|---|---|---|---|---|
| | 1 | 3 | 10 | 30 | 100 | 300 |
| Compound 1 | | | 16 | 53 | 22 | 5 / 17 |
| Compound 10 | 10 | 41 | 28 | 16 | 3 | |
| Aniracetam | | | 9 | 23 | 29 | 5 |

TEST EXAMPLE 2

Acute toxicity test

Mice (ddY, five-week-old males) were used in groups of 4 to 5 mice each. The test compound was dissolved or suspended in 0.5% solution of sodium carboxymethyl cellulose and administered orally. The mice were observed for 3 days to measure the number of deaths. Compound 1 was 3000 mg/kg in $LD_{50}$ and Compound 10 was >3000 mg/kg in $LD_{50}$.

Industrial applicability

The medicaments for treating senile dementia must have cerebral function improving activity to ameliorate memory and learning disturbances and activity to activate the metabolism of cerebral nerve cells or to protect these cells from injuries and attacks. It is further desired that the medicaments be diminished in side effects and of high safety since the patients are aged people. When fulfilling these requirements, the medicaments are useful for treating senile dementia.

Table 2 reveals that the present compound exhibit antiamnesia activity and further have two activities, i.e., activity to improve cerebral functions and activity to activate cerebral metabolism or protect anoxic brain damage.

To sum up, the present compounds have two pharmacological activities, i.e., cerebral function improving activity and cerebral metabolism activating or anoxic brain damage protecting activity, low toxicity and therefore usefulness and are effective for treating senile dementia.

We claim:

1. A diazabicycloalkane derivative represented by the formula

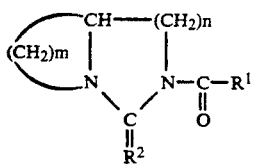

wherein $R^1$ is a phenyl group, thienyl group or furyl group, the phenyl group may have a lower alkoxyl, a lower alkyl or a halogen atom as a substituent, $R^2$ is an oxygen atom or a sulfur atom, m is 3 or 4, and n is 1 or 2, provided that when m is 4 and n is 1, $R^1$ is not a phenyl group.

2. A diazabicycloalkane derivative as defined in claim 1 wherein $R^1$ is a phenyl group having or not having 1 to 3 substituents selected from among lower alkoxyl, lower alkyl and halogen atom.

3. A diazabicycloalkane derivative as defined in claim 2 wherein $R^2$ is oxygen atom.

4. A diazabicycloalkane derivative as defined in claim 2 wherein $R^2$ is sulfur atom.

5. A diazabicycloalkane derivative as defined in claim 2 wherein $R^1$ is a phenyl group having one lower alkoxyl as a substituent, m is 3 and n is 2.

6. A diazabicycloalkane derivative as defined in claim 1 which is hexahydropyrrolo[1,2-c]pyrimidine-2-(4-methoxybenzoyl)-1-(12H)-one or hexahydropyrrolo[1,2-c]pyrimidine-2-(4-methoxybenzoyl)-1-(12H)-thione.

7. A cerebral function improving composition and a cerebral metabolism activating or anoxic brain damage protecting composition each comprising a pharmacologically acceptable carrier and an effective amount of a diazabicycloalkane derivative represented by the formula

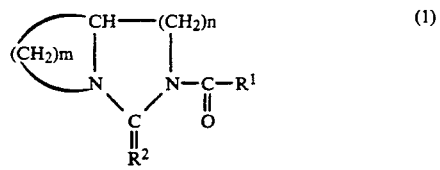

wherein $R^1$ is a phenyl group, a thienyl group or a furyl group, the phenyl group may have a lower alkoxyl, a lower alkyl or a halogen atom as a substituent, $R^2$ is an oxygen atom or a sulfur atom, m is 3 or 4, and n is 1 or 2, provided that when m is 4 and n is 1, $R^1$ is not a phenyl group.

8. A method of improving cerebral functions and activating cerebral metabolism or protecting anoxic brain damage characterized by administering to a patient an effective amount of the diazabicycloalkane derivative represented by the formula

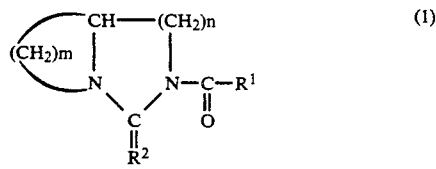

wherein $R^1$ is a phenyl group, a thienyl group or a furyl group, the phenyl group may have lower alkoxyl, lower alkyl or halogen atom as a substituent, $R^2$ is an oxygen atom or a sulfur atom, m is 3 or 4, and n is 1 or 2, provided that when m is 4 and n is 1, $R^1$ is not a phenyl group.

9. A diazabicycloalkane derivative as defined in claim 2, wherein $R^1$ is a p-methoxyphenyl group, m is 4 and n is 1.

* * * * *